(12) United States Patent
Suzuki et al.

(10) Patent No.: US 7,105,258 B2
(45) Date of Patent: Sep. 12, 2006

(54) CHARGE TRANSPORT MONOMER, CHARGE TRANSPORT MATERIAL, AND PROCESS FOR PRODUCING THE SAME

(75) Inventors: Satoshi Suzuki, Tokyo-To (JP); Masato Okada, Tokyo-To (JP); Yoshinobu Kashibuchi, Hiratsuka (JP); Tohru Kobayashi, Hiratsuka (JP)

(73) Assignees: Dai Nippon Printing Co., Ltd., Shinjuku-Ku (JP); Takasago International Corporation, Ohta-Ku (JP)

( * ) Notice: Subject to any disclaimer, the term of this patent is extended or adjusted under 35 U.S.C. 154(b) by 0 days.

(21) Appl. No.: 10/984,356

(22) Filed: Nov. 9, 2004

(65) Prior Publication Data

US 2005/0118521 A1    Jun. 2, 2005

(30) Foreign Application Priority Data

Nov. 11, 2003  (JP) ............................. 2003-381736

(51) Int. Cl.
    *G03G 5/07*    (2006.01)
    *C09K 11/06*   (2006.01)
    *C08F 134/04*  (2006.01)
    *C08F 132/08*  (2006.01)
    *C07D 209/82*  (2006.01)

(52) U.S. Cl. ..................... 430/79; 428/917; 252/301.6; 526/259; 526/280; 526/256; 548/440; 548/441; 548/444

(58) Field of Classification Search .................. 430/79; 428/917; 252/301.16; 526/259, 280, 256; 548/440, 441, 444
    See application file for complete search history.

(56) References Cited

U.S. PATENT DOCUMENTS

2004/0258953 A1    12/2004  Kido et al.

FOREIGN PATENT DOCUMENTS

| JP | 2002-302516 | 10/2002 |
|----|-------------|---------|
| JP | 2004-018787 | 1/2004  |
| JP | 2004-185967 | 7/2004  |
| JP | 2004-217837 | 8/2004  |
| JP | 2004-220986 | 8/2004  |
| WO | 03/074628   | 9/2003  |
| WO | WO-03/074628 A1 * | 9/2003 |

* cited by examiner

*Primary Examiner*—Kamal A. Saeed
*Assistant Examiner*—Joseph R. Kosack
(74) *Attorney, Agent, or Firm*—Burr & Brown

(57) ABSTRACT

There is provided a charge transport material which can easily be coated to form a film, is less likely to be crystallized during or after film formation, has excellent charge transport capability, and high applicability to electronic devices. A charge transport monomer comprising conventional CBP with a specific substituent introduced thereinto is polymerized to prepare a polymer which is brought to a charge transport material comprising this polymer.

4 Claims, 2 Drawing Sheets

CHARGE TRANSPORT MONOMER, CHARGE TRANSPORT MATERIAL, AND PROCESS FOR PRODUCING THE SAME

This application claims the benefit of Japanese Application 2003-381736, filed Nov. 11, 2003, the entirety of which is incorporated herein by reference.

BACKGROUND OF THE INVENTION

1. Field of the Invention

The present invention relates to a charge transport material that can be applied to organic electronic devices such as electrophotographic photoreceptors, organic electroluminescent elements, photorefractive elements, electrochromic elements, photosensors, and solar cells. More particularly, the present invention relates to a charge transport material having excellent charge transport capability and a process for producing the same.

2. Background Art

Charge transport materials are materials having such a charge transport capability that, upon charge injection, charge is diffused and moved, for example, due to charge concentration gradient and electric field gradient. A material which functions to transport electron as the charge is called an electron transport material, and a material which functions to transport hole as the charge is called a hole transport material. The electron transport material and the hole transport material are collectively called a charge transport material. The charge transport material has been extensively studied as a material indispensable for the preparation of organic electronic devices such as electrophotographic photoreceptors, organic electroluminescent elements, photorefractive elements, electrochromic elements, photosensors, and solar cells.

Basic properties required of the charge transport material include charge acceptability for electron or hole or both electron and hole in a neutral state, a high charge transport capability, good film formability, and a stable amorphous state of the film.

The charge transport material is in many cases used as an even thin film. Therefore, it is important that a film be easily formed from the charge transport material. When a thin film having a thickness of not more than 1 µm is formed using a charge transport material of a low molecular compound, vacuum deposition is generally used for film formation. The vacuum deposition requires a larger deposition apparatus than coating methods, leading to an increase in cost. In the vacuum deposition, the adoption of a large-area substrate on which the charge transport layer is to be formed is difficult. Further, when the low molecular compound is used solely as the charge transport material, for example, the mechanical strength and heat stability of the formed thin film are unsatisfactory. For this reason, a method is also adopted in which a polymer is used as a binder and the low molecular compound is dispersed in a binder to prepare a coating liquid which is then coated to form a film.

Incidentally, most of charge transport materials are hole transport materials, and tertiary amine derivatives such as triarylamine have extensively been used as hole transport materials. On the other hand, for the electron transport material, for example, since the solubility thereof in organic solvents is not high, the electron transport material is not suitable for the formation of a film by coating. Further, the mobility of electron is not high. For the above reason, as compared with the hole transport material, the number of types of the electron transport material is smaller.

Some of charge transport materials are bipolar charge transport materials that have both a hole transport function and an electron transport function. An example of a bipolar charge transport material is CBP (4,4-bis(carbazol-9-yl)-biphenyl) (see, for example, Japanese Patent Laid-Open No. 168443/1998). This CBP has a bipolar property and, in addition, can form a highly transparent thin film and is highly compatible with a luminescent dopant. Therefore, CBP is suitable for use in the formation of a charge transport layer in organic electroluminescent elements and thus has been suitably used in organic electroluminescent elements using a phosphorescent dopant (M. A. Baldo et al., Nature, vol. 395, p. 151 (1998), M. A. Baldo et al., Applied Physics Letters, vol. 75, p. 4 (1999), M. A. Baldo et al, Nature, vol. 403, p. 750 (2000)).

In charge transport materials such as CBP, however, vacuum deposition has still mainly been used for film formation. Further, since CBP molecules are likely to take a planar structure, an amorphous film formed of CBP is likely to be crystallized with the elapse of time or upon heating. For this reason, the application of CBP to electronic devices involving generation of heat due to Joule's heat, particularly such as organic electroluminescent elements, requires doping of CBP with a large amount (about 5 to 10% by mass) of a dopant, or the use of a binder to prevent crystallization of CBP. Therefore, when CBP is solely used, a film cannot be formed by coating without difficulties.

SUMMARY OF THE INVENTION

In view of the above problems of the prior art, the present invention has been made, and an object of the present invention is to provide a charge transport material which can easily be coated to form a film, is less likely to be crystallized during or after film formation, has excellent charge transport capability, and high applicability to electronic devices.

According to the present invention, there is provided a charge transport monomer (hereinafter often abbreviated to "monomer") represented by formula (I):

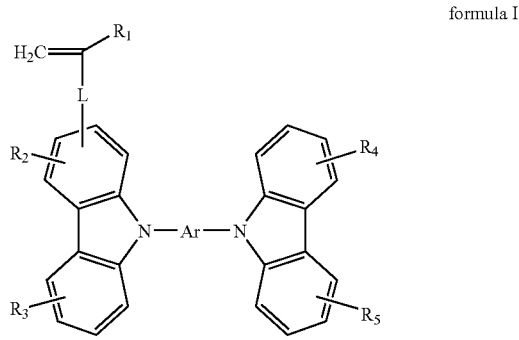

formula I wherein

Ar represents an unsubstituted or substituted arylene group having 6 to 60 carbon atoms involved in conjugation or an unsubstituted or substituted heterocyclic compound group having 4 to 60 carbon atoms involved in conjugation;

L represents a divalent hydrocarbon or hetero-atom-containing hydrocarbon group which may be branched or contain a cyclic structure; and $R_1$ to $R_5$ each independently represent a group selected from the group consisting of a hydrogen atom, an alkyl group having 1 to 20 carbon atoms, an alkoxy group having 1 to 20 carbon atoms, an aryl group having 6 to 60 carbon atoms, an aryloxy group having 6 to 60 carbon atoms, an arylalkyl group having 7 to 60 carbon atoms, an arylalkoxy group having 7 to 60 carbon atoms, a heterocyclic compound group having 4 to 60 carbon atoms, a cyano group, a nitro group, and a halogen atom.

According to another aspect of the present invention, there is provided a charge transport material comprising a polymer containing at least one monomer unit of the above type.

According to another aspect of the present invention, there is provided a process for producing a charge transport material, comprising the step of polymerizing the above monomer either alone or together with other monomer.

The monomer according to the present invention can easily be polymerized to prepare a polymer. The polymer comprising units of this monomer can be coated to form an even thin film without doping or the use of any binder. Therefore, as compared with electronic devices prepared using conventional CBP as a charge transport material, electronic devices, which have higher stability and more inexpensive, can be realized.

Further, according to the charge transport material of the present invention, a charge transport capability suitable for the purpose can be imparted by varying the content of charge transport monomer units. Further, the charge transport capability can be regulated by varying the type of the charge transport monomer or by preparing a copolymer using a combination of two or more different charge transport monomers. Further, the charge transport monomer according to the present invention can be copolymerized with other suitable monomer to improve coatability of the copolymer (charge transport material) or to optimize the form of the film or electrical properties.

DETAILED DESCRIPTION OF THE INVENTION

Figure 1:
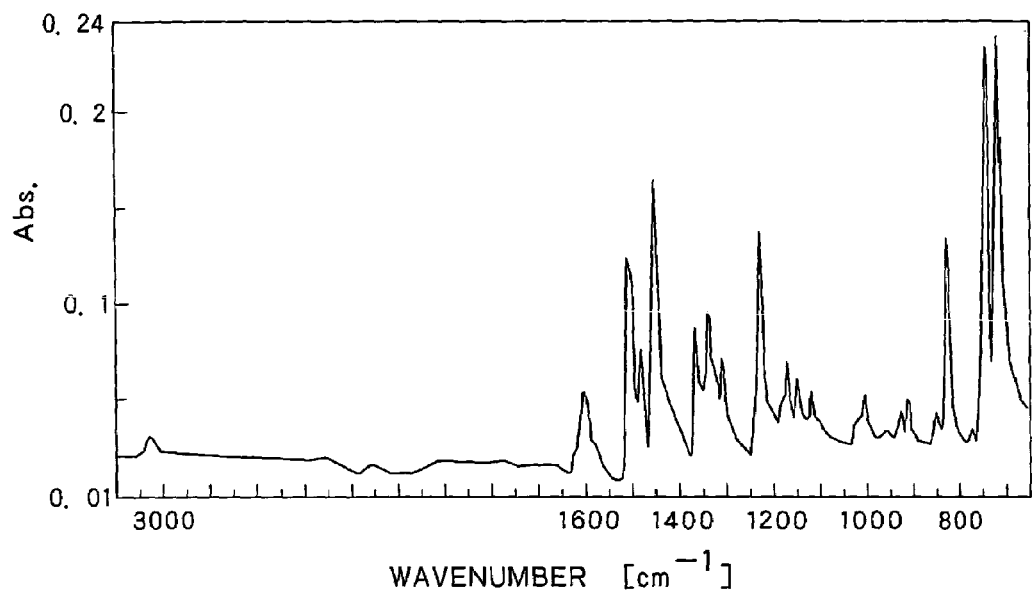
FIG. 1 is an infrared (IR) spectrum of CBP as a comparative reference material.

The charge transport monomer according to the present invention represented by formula (I) will be first described.

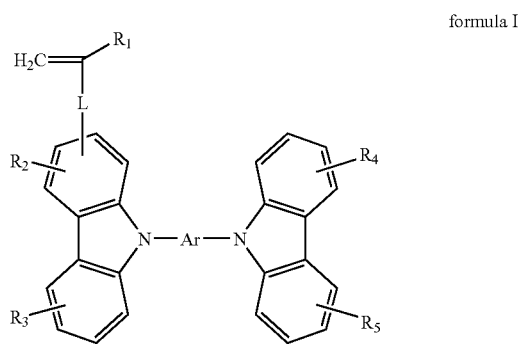

formula I

In formula (I), Ar represents an arylene group having 6 to 60 carbon atoms involved in conjugation or a heterocyclic compound group having 4 to 60 carbon atoms involved in conjugation. Specifically, examples of Ar include aromatic compound groups represented by formulae (a) to (g) or derivative groups thereof.

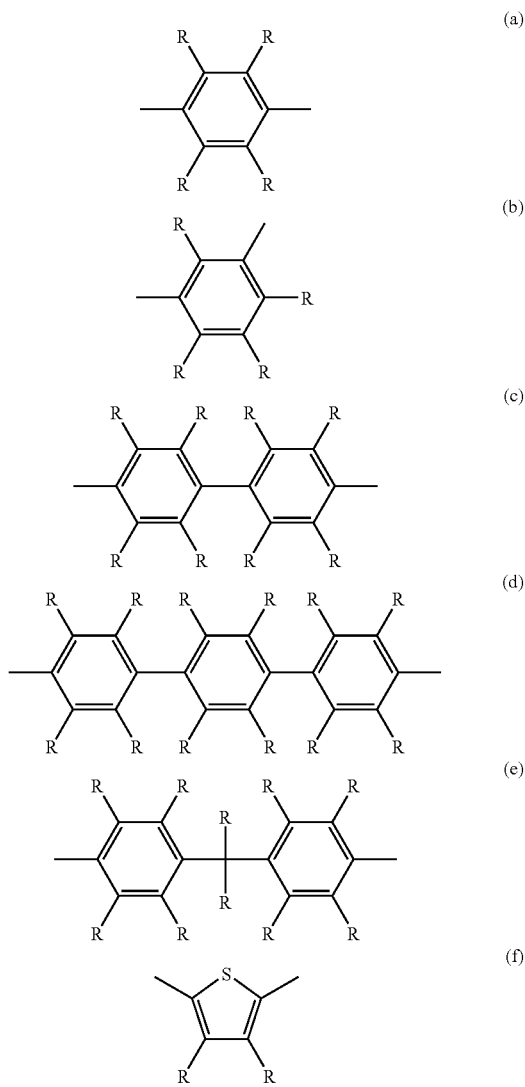

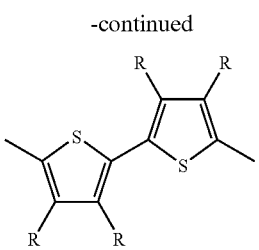

(g)

When a heterocyclic or hetero-atom-containing aromatic group is used, the reduction potential or triplet state energy level is likely to be lower than the energy level of phosphorescence dopant. For this reason, there is a possibility that the heterocyclic or hetero-atom-containing aromatic group lacks in compatibility with the phosphorescence dopant. Therefore, among the above groups (a) to (g), a 1,4-phenylene, 4,4'-biphenylene, or 4,4"-terphenylene group or a derivative group of any of these groups is preferred.

R in formulae (a) to (g) and $R_1$ to $R_5$ in formula (I), which may be the same or different, represent a group selected from the group consisting of a hydrogen atom, an alkyl group having 1 to 20 carbon atoms, an alkoxy group having 1 to 20 carbon atoms, an aryl group having 6 to 60 carbon atoms, an aryloxy group having 6 to 60 carbon atoms, an arylalkyl group having 7 to 60 carbon atoms, an arylalkoxy group having 7 to 60 carbon atoms, a heterocyclic compound group having 4 to 60 carbon atoms, a cyano group, a nitro group, and a halogen atom.

Alkyl groups having 1 to 20 carbon atoms include methyl, ethyl, n-propyl, i-propyl, n-butyl, i-butyl, sec-butyl, t-butyl, n-hexyl, n-octyl, nonyl, decyl, and lauryl groups. Among them, pentyl, hexyl, octyl, and decyl groups are preferred, because they have no significant influence on the energy level of a charge transport material comprising a polymer comprising charge transport monomer units according to the present invention, and, in addition, the solubility of the charge transport material in an organic solvent can be easily ensured.

Alkoxy groups having 1 to 20 carbon atoms include methoxy, ethoxy, propyloxy, butoxy, pentyloxy, hexyloxy, heptyloxy, octyloxy, nonyloxy, decyloxy, and lauryloxy groups. Among them, pentyloxy, hexyloxy, octyloxy, and decyloxy groups are preferred, because they have no significant influence on the energy level of a charge transport material comprising a polymer comprising charge transport monomer units according to the present invention, and, in addition, the solubility of the charge transport material in an organic solvent can be easily ensured.

Aryl groups having 6 to 60 carbon atoms include phenyl, $C_1$–$C_{12}$ alkoxyphenyl (wherein $C_1$–$C_{12}$ means that the number of carbon atoms is 1 to 12; the same shall apply hereinafter), $C_1$–$C_{12}$ alkylphenyl, 1-naphthyl, and 2-naphthyl groups. Among them, $C_1$–$C_{12}$ alkoxyphenyl and $C_1$–$C_{12}$ alkylphenyl groups are preferred, because they have no significant influence on the energy level of a charge transport material comprising a polymer comprising charge transport monomer units according to the present invention, and, in addition, the solubility of the charge transport material in an organic solvent can be easily ensured.

Aryloxy groups having 6 to 60 carbon atoms include phenoxy, $C_1$–$C_{12}$ alkoxyphenoxy, $C_1$–$C_{12}$ alkylphenoxy, 1-naphthyloxy, and 2-naphthyloxy groups. Among them, $C_1$–$C_{12}$ alkoxyphenoxy and $C_1$–$C_{12}$ alkylphenoxy groups are preferred.

Arylalkyl groups having 7 to 60 carbon atoms include phenyl-$C_1$–$C_{12}$ alkyl, $C_1$–$C_{12}$ alkoxyphenyl-$C_1$–$C_{12}$ alkyl, $C_1$–$C_{12}$ alkylphenyl-$C_1$–$C_{12}$ alkyl, 1-naphthyl-$C_1$–$C_{12}$ alkyl, and 2-naphthyl-$C_1$–$C_{12}$ alkyl groups. Among them, $C_1$–$C_{12}$ alkoxyphenyl-$C_1$–$C_{12}$ alkyl and $C_1$–$C_{12}$ alkylphenyl-$C_1$–$C_{12}$ alkyl groups are preferred, because they have no significant influence on the energy level of a charge transport material comprising a polymer comprising charge transport monomer units according to the present invention, and, in addition, the solubility of the charge transport material in an organic solvent can be easily ensured.

Arylalkoxy groups having 7 to 60 carbon atoms include phenyl $C_1$–$C_{12}$ alkoxy, $C_1$–$C_{12}$ alkoxyphenyl-$C_1$–$C_{12}$ alkoxy, $C_1$–$C_{12}$ alkylphenyl-$C_1$–$C_{12}$ alkoxy, 1-naphthyl-$C_1$–$C_{12}$ alkoxy, and 2-naphthyl-$C_1$–$C_{12}$ alkoxy groups. Among them, the $C_1$–$C_{12}$ alkylphenyl-$C_1$–$C_{12}$ alkoxy group is preferred.

Heterocyclic compound groups having 4 to 60 carbon atoms include thienyl, $C_1$–$C_{12}$ alkylthienyl, pyrrolyl, furyl, pyridyl, and $C_1$–$C_{12}$ alkylpyridyl groups. Among them, $C_1$–$C_{12}$ alkylthienyl and $C_1$–$C_{12}$ alkylpyridyl groups are preferred, because they have no significant influence on the energy level of a charge transport material comprising a polymer comprising charge transport monomer units according to the present invention, and, in addition, the solubility of the charge transport material in an organic solvent can be easily ensured.

Halogen atoms include fluorine, chlorine, bromine, and iodine atoms.

Among the examples of R, alkyl-containing substituents may be straight chain, branched chain, or cyclic substituents or a combination of these substituents. Alkyl-containing substituents, which are not straight chain, include, for example, isoamyl, 2-ethylhexyl, 3,7-dimethyloctyl, cyclohexyl, and 4-$C_1$–$C_{12}$ alkylcyclohexyl groups.

Further, at least one of R in formulae (a) to (g) and $R_1$ to $R_5$ in formula (I) may or may not combine together to form a saturated or unsaturated five- or six-membered ring. Specific examples of the case where the saturated or unsaturated six-membered ring is formed are as follows.

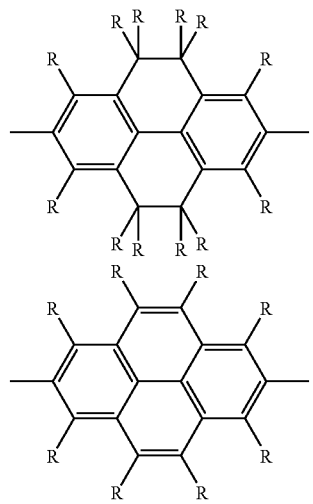

In order that the polymer (including copolymer) comprising the charge transport monomer represented by formula (I) is soluble in an organic solvent, the polymer preferably contains a plurality of R substituents. Among the above group of substituents, the alkyl or alkoxy group is particularly preferably contained in the polymer because these groups have no significant influence on the energy level of the charge transport material.

In formula (I), L represents a divalent hydrocarbon group or hetero-atom-containing hydrocarbon group which may be branched or may have a cyclic structure. Preferably, for example, from the viewpoint of ensuring film forming properties, mechanical strength, and charge transport capability, these hydrocarbon groups contain a linking group selected from a straight-chain alkyl bond, an ether bond, an ester bond, a carbonate bond and the like and have 20 or less carbon atoms. Specific examples of L are as follows.

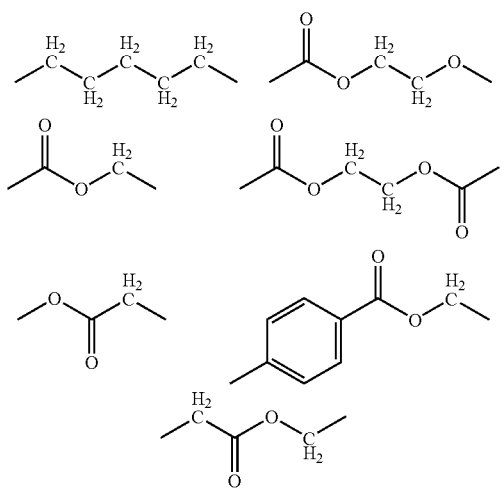

The glass transition temperature, the degree of crystallization, the refractive index, adhesion, solubility and the like can be regulated while maintaining the charge transport capability of the charge transport material (polymer) of the present invention by changing the constituent of L in formula (I). A highly functional organic EL element can be realized by regulating these various functions.

The charge transport monomer according to the present invention can be synthesized by a conventional method, for example, by the following process.

A compound represented by formula (II) is first synthesized:

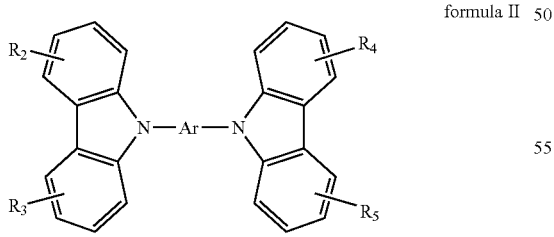

formula II wherein Ar and $R_2$ to $R_5$ are as defined above. This compound may be synthesized by a conventional method (for example, Japanese Patent Laid-Open No. 168443/1998). Next, a functional group, for example, an amino group, a hydroxyl group, a hydroxyalkyl group such as a methylol group, a carboxyl group, a sulfonyl group, an epoxy group, or an isocyanate group, is introduced into the above compound. Next, a monomer represented by formula (I) is prepared by introducing a vinyl compound having a group reactive with the above functional group into the above compound. Vinyl-containing compounds include, for example, (meth)acrylic acid, (meth)acrylamide, (meth)acrylic acid chloride, (meth)acrylic acid anhydride, hydroxyalkyl (meth)acrylate, and glycidyl ether (meth)acrylate. This production process is merely one example of possible production processes, and the monomer may be synthesized by other production process.

Specific examples of polymers (charge transport materials) prepared from the above monomer include polymers represented by the following formulae.

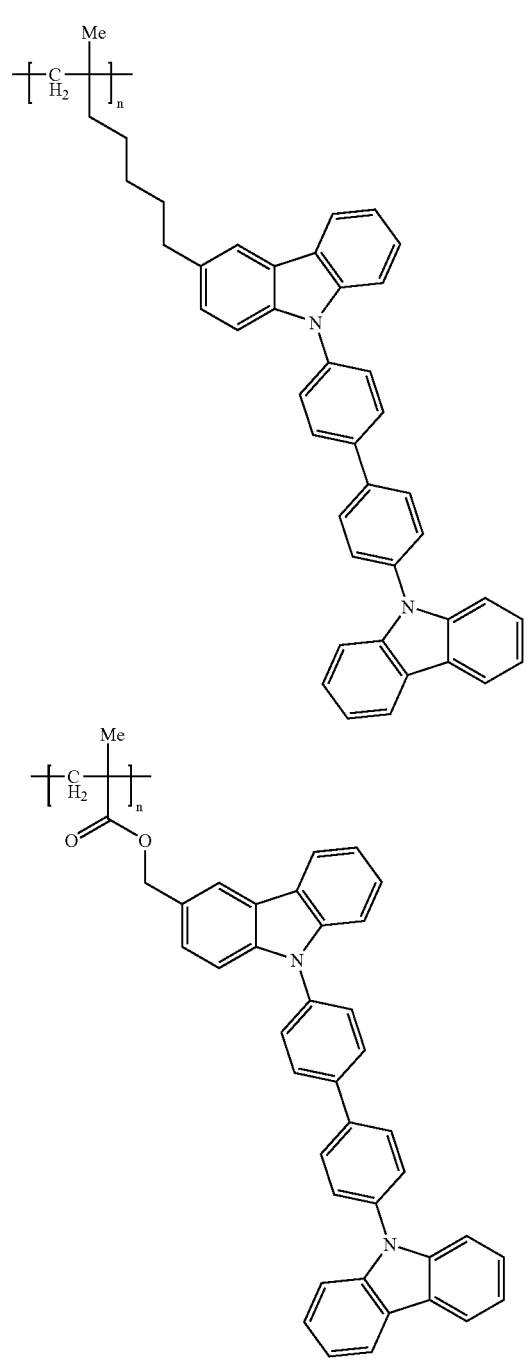

-continued
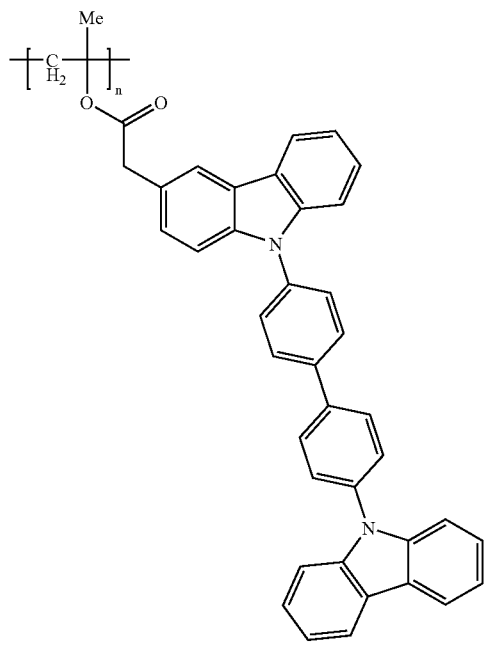
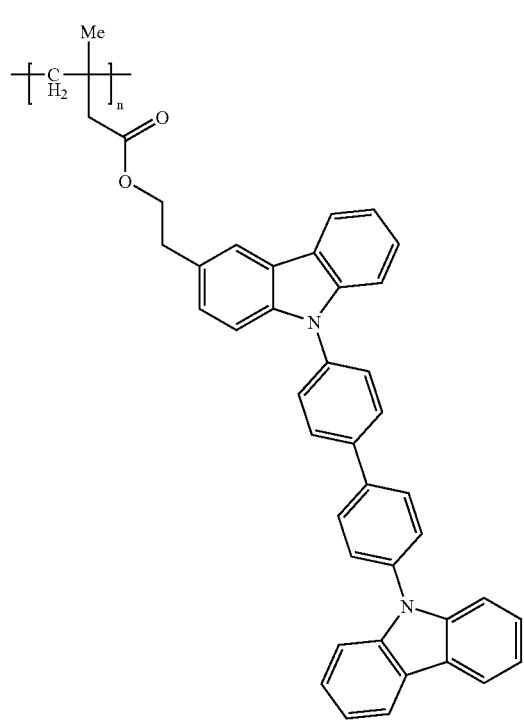
-continued
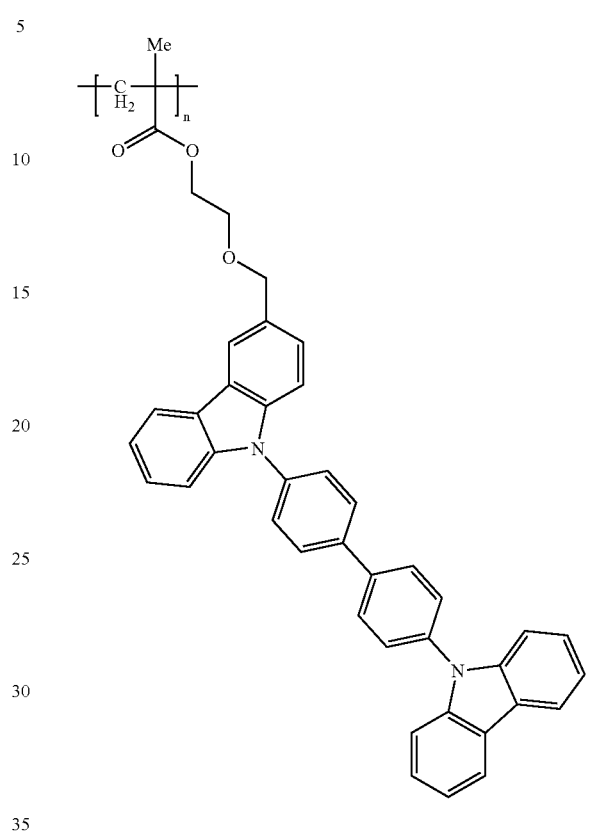
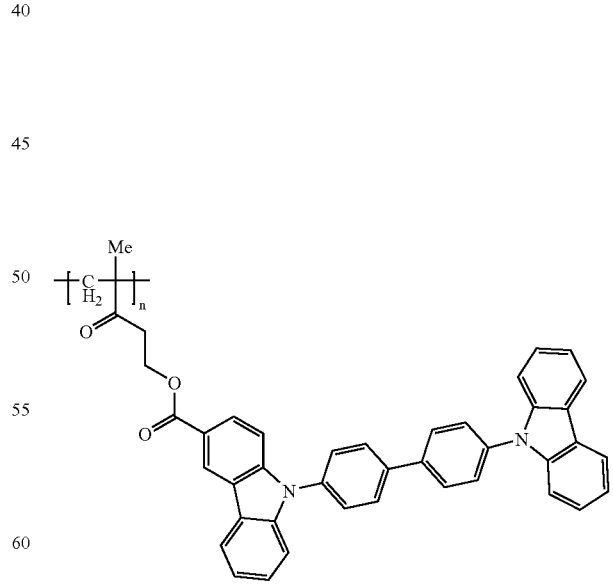

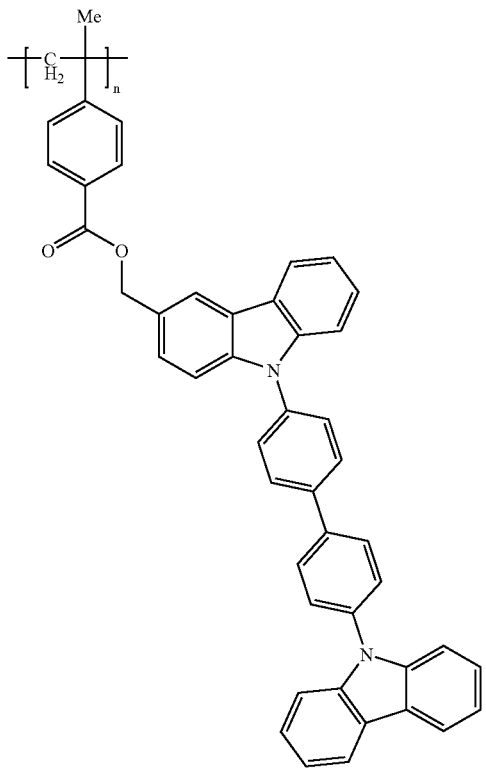

wherein n is an integer of 2 or more.

The charge transport material (polymer) according to the present invention is a polymer comprising at least one monomer unit, represented by formula (I), per molecule, preferably a polymer comprising 5 to 100,000 monomer units per molecule. The charge transport material (polymer) according to the present invention may be a homopolymer of the above monomer, or alternatively may be a copolymer of the above monomer with other monomer. In the case of the copolymer, the form of the copolymer may be alternate, random, block, or graft. Alternatively, the copolymer may be a polymer having a structure intermediate between these structures, for example, a random copolymer having a structure which is somewhat similar to the block copolymer.

Other monomers copolymerized with the above monomer are not particularly limited. Preferably, however, these other monomers have a structure which does not lower the solubility of the resultant polymer in organic solvents and has a charge transport capability.

A specific example of preferred copolymers is a copolymer with a styrenic monomer, and the use of this copolymer can improve the solubility in organic solvents. Specifically, copolymers represented by the following formula may be mentioned as such copolymers.

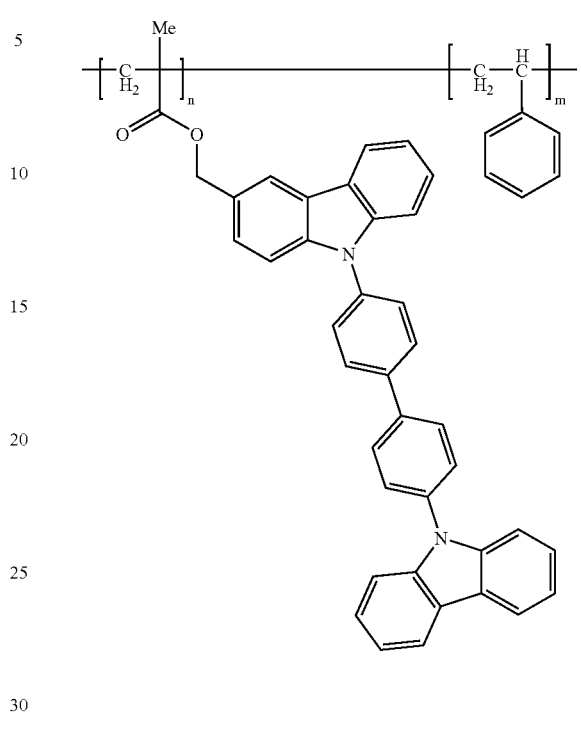

wherein n and m each are an integer of 1 or more.

Additional examples of such copolymers include copolymers with a monomer having a triphenylamine structure with a hole transport function represented by the following formula.

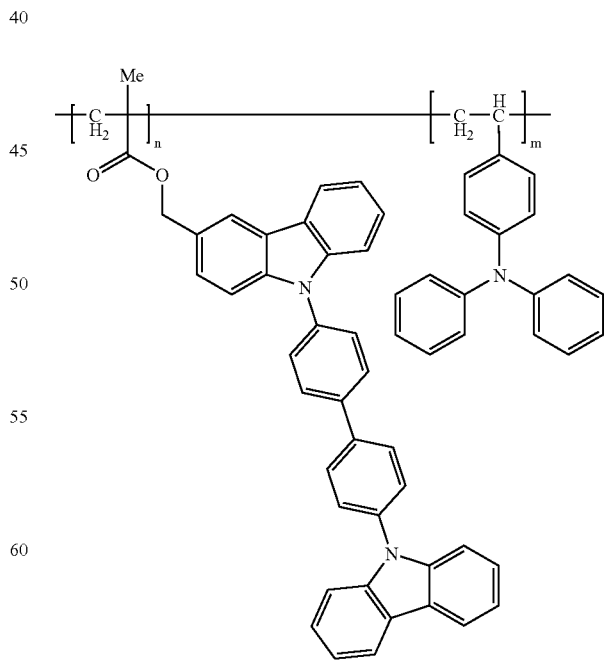

wherein n and m each are an integer of 1 or more.

The content of the monomer unit constituting the polymer according to the present invention is preferably 50 to 100% by mole, more preferably 70 to 100% by mole, based on 100% by mole of the total amount of all the monomer units. When the content of the monomer unit is less than 50% by mole, the content of the monomer unit as the charge transport unit is so low that the charge transport capability of the polymer cannot be maintained.

The degree of polymerization of the polymer according to the present invention depends upon the structure and content of the monomer. Preferably, however, the degree of polymerization of the polymer is $10^3$ to $10^8$ as determined using polystyrene as a standard. More preferably, the degree of polymerization is $10^4$ to $10^6$ from the viewpoints of solubility in solvents and film forming properties. The molecular weight refers to the number average molecular weight determined by gel permeation chromatography (GPC) (solvent: chloroform) using polystyrene as a standard. The charge transport monomer represented by formula (I) may be polymerized or copolymerized with other monomer by any polymerization method without particular limitation. For example, radical polymerization, ion polymerization, and coordination polymerization may be used. Among them, radical polymerization is preferred. Initiators for the radical polymerization include, for example, azo compounds and peroxides. Specifically, azobisisobutyronitrile, azobisisobutyric acid diester derivatives or benzoyl peroxide are suitable.

Any solvent can be used in the polymerization without particular limitation, and examples thereof include aromatic hydrocarbons (for example, benzene and toluene), halogenated hydrocarbons (for example, dichloroethane and chloroform), ethers (for example, tetrahydrofuran and dioxane), amides (for example, diethylformamide and dimethylacetamide), esters (for example, ethyl acetate), alcohols (for example, methanol), and ketones (for example, acetone and cyclohexanone). Solution polymerization in which polymerization is carried out in a homogeneous system and precipitation polymerization in which the resultant polymer is precipitated may also be utilized by selecting a proper solvent.

When these polymers are used as a charge transport material for organic electronic devices, the purity of the polymer affects charge transport properties and the stability of the amorphous state of the film. Therefore, the synthesis of the polymer is preferably followed by purification treatment such as reprecipitation or fractionation by chromatography.

Since the charge transport material according to the present invention is soluble in a solvent, a film may be formed using a solution containing a charge transport material (a coating liquid). Good solvents for the charge transport material include, for example, chloroform, methylene chloride, dichloroethane, tetrahydrofuran, and toluene. In general, the solubility of the charge transport material according to the present invention in the above solvent is not less than 0.1% by mass although the solubility varies depending upon the structure and molecular weight of the polymer constituting the charge transport material. In the production of an electronic device, a charge transport layer can be formed simply by coating a solution (coating liquid) of the charge transport material in the organic solvent on a substrate and then drying the coating to remove the solvent. Therefore, an electronic device can be produced in a simple and cost-effective manner.

In the formation of the charge transport layer, the charge transport material according to the present invention and other charge transport material can be simultaneously used. Other charge transport materials, that is, electron transport materials or hole transport materials, are not particularly limited and may be conventional ones. Hole transport materials include, for example, pyrazoline derivatives, arylamine derivatives, stilbene derivatives, and triphenyldiamine derivatives. Electron transport materials include, for example, oxadiazole derivatives, anthraquinodimethane or its derivatives, benzoquinone or its derivatives, naphthoquinone or its derivatives, anthraquinone or its derivatives, tetracyanoanthraquinodimethane or its derivatives, fluorenone derivatives, diphenyldicyanoethylene or its derivatives, diphenoquinone derivatives, and metal complexes of 8-hydroxyquinoline or its derivatives. They may be used either solely or as a mixture of two or more of them. Any one of the electron transport compound and the hole transport compound may be used, or alternatively both the electron transport compound and the hole transport compound may be simultaneously used.

The organic solvent solution is preferably coated by a coating method, for example, spin coating, cast coating, dip coating, die coating, bead coating, bar coating, roll coating, spray coating, gravure coating, flexo printing, screen printing, or offset printing. When the film is formed by the coating method, preferably, heat drying at 30 to 300° C., preferably 60 to 200° C., under reduced pressure or in an inert atmosphere is carried out to remove the solvent.

EXAMPLES

The following Examples further illustrate but do not limit the present invention.

Measuring instruments and measuring conditions used for synthesis are as follows.

(1) $^1$H-NMR: DRX-500 apparatus (500 MHz) manufactured by BRUKER, internal reference material=tetramethylsilane, as measured in deutrochloroform (2) IR: Fourier transformation infrared spectrophotometer FT/IR-610 apparatus (manufactured by Japan Spectroscopic Co., Ltd.)

(3) MASS: Hitachi M-80B (manufactured by Hitachi, Ltd.)

(4) Molecular weight: measured by GPC (two columns of Shodex GPC (K806M) being connected to each other); determined using polystyrene as a standard in chloroform solvent Synthesis of Charge Transport Material 1

A 2-L Kolben equipped with a stirrer and a drain device was charged under a nitrogen stream with 150 g (369.5 mmol) of 4,4'-diiodobiphenyl, 123.5 g (738.6 mmol) of carbazole, 23 g of copper powder, 100 g of potassium carbonate, and 500 ml of 1,3-diisopropylbenzene. The mixture was heated under reflux for 30 hr and was allowed to cool. Toluene was then added, and the mixture was filtered. The solvent in the filtrate was distilled off under reduced pressure. Methanol (500 ml) was added to the residue to precipitate crystals. The crystals were collected by filtration to give CBP (4,4'-bis(carbazol-9-yl)-biphenyl) (122.8 g, yield 68.6%).

A 200-ml Kolben equipped with a stirrer and a condenser was charged under a nitrogen stream with 60 g (123.8 mmol) of CBP prepared above, 337 g (2475 mmol) of N,N-dimethylformamide, and 750 ml of chloroform. The mixture was heated on a warm water bath to 60° C., and 190 g (1239.4 mmol) of phosphorus oxychloride was added dropwise to the above mixture. After the dropwise addition, the mixture was heated with stirring for 8 hr. This reaction solution was poured into an aqueous sodium carbonate solution. The organic layer was washed with water, and the solvent was distilled off. The residue was subjected to fractionation by column chromatography on silica gel (eluent: toluene) to give 4-(carbazol-9-yl)-4'-(3-formylcarbazol-9-yl)-biphenyl (23 g, yield 36.2%).

A 100-ml Kolben equipped with a stirrer and a condenser was charged under a nitrogen stream with 18 g (15.6 mmol) of 4-(carbazol-9-yl)-4'-(3-formylcarbazol-9-yl)-biphenyl prepared above and 800 ml of tetrahydrofuran. Sodium tetrahydroborate (0.65 g, 17.2 mmol) was introduced at room temperature into the above mixture, and the mixture was stirred for one hr. Thereafter, 160 ml of methanol was introduced into the reaction solution, and the mixture was stirred for 3 hr. The solvent was distilled off, and the residue was dissolved in 500 ml of toluene. The solution was washed with water, and the solvent was then distilled off to give 4-(carbazol-9-yl)-4'-(3-hydroxymethylcarbazol-9-yl)-biphenyl (7.9 g, yield 98.4%).

A 100-ml Kolben equipped with a stirrer and a condenser was charged under a nitrogen stream with 7.5 g (14.6 mmol) of 4-(carbazol-9-yl)-4'-(3-hydroxymethylcarbazol-9-yl)-biphenyl, 2.7 g (17.5 mmol) of methacrylic acid anhydride, 500 ml of toluene, 0.2 g of dimethylaminopyridine, and 2.5 g of triethylamine, and the mixture was stirred at room temperature for 20 hr. Methanol (30 ml) was added to the mixture, followed by stirring for one hr. An aqueous dilute sulfuric acid solution was then added thereto. The organic layer was separated and was then washed with water, and the solvent was distilled off. Methanol was added to the residue to precipitate crystals. The crystals were collected by filtration and was purified by column chromatography on silica gel (eluent: toluene) to give monomer A represented by the following formula (8 g, yield 94.0%).

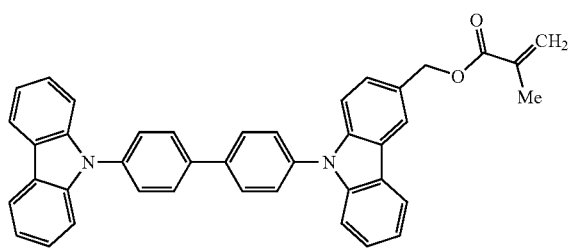

The results of analysis were as follows.

$^1$H NMR: 1.98 (s, 3H), 5.40 (s, 2H), 5.57 (s, 1H), 7.29–7.36 (m, 3H), 7.41–7.54 (m, 8H), 7.67–7.72 (m, 4H), 7.89–7.93 (m, 4H), 8.15–8.23 (m, 4H).

A 200-ml Kolben was charged with 7.5 g (12.8 mmol) of monomer A and 150 ml of toluene under a nitrogen stream. The mixture was heated on a warm water bath to 80° C., and 0.15 g (0.9 mmol) of azobisisobutyronitrile was introduced into the mixture. A polymerization was allowed to react with stirring for 5 hr. After the completion of the reaction, the reaction solution was allowed to cool. This reaction solution was added dropwise to acetone. The resultant precipitate was collected by filtration and was washed with acetone to give 4.5 g of charge transport material 1 of the present invention represented by the following formula.

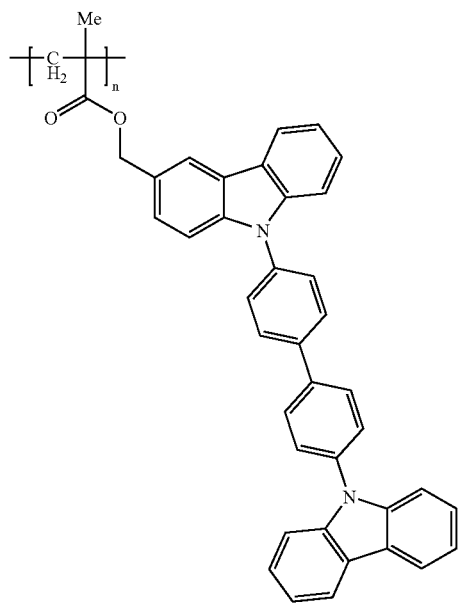

wherein n is a number which provides a molecular weight of 10,000.

Figure 2:
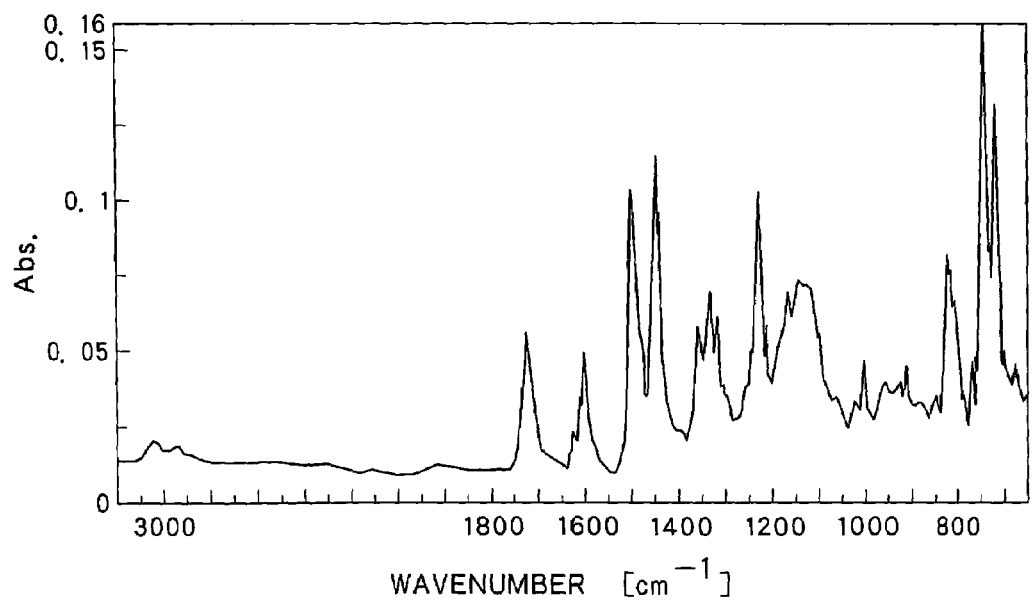
FIG. 2 is an IR spectrum of a charge transport material 1.

An IR spectrum of CBP as a comparative reference material is shown in FIG. 1, and an IR spectrum of the charge transport material 1 is shown in FIG. 2. The IR spectrum of charge transport material 1 had the following main absorption peaks.

3,042 cm$^{-1}$: stretching of aromatic C—H (derived from CBP unit); 2,946 cm$^{-1}$: stretching of alkane C—H (derived from polymer main chain); 1,726 cm$^{-1}$: stretching of saturated fatty ester C=O; 1,503 cm$^{-1}$: stretching of n-aromatic C=C (derived from CBP unit); 1,200–1,100 cm$^{-1}$: stretching of saturated fatty ester C—O; 746 cm$^{-1}$: out-of-plane deformation vibration of polycyclic aromatic C—H (derived from CBP unit); and 722 cm$^{-1}$: out-of-plane deformation vibration of polycyclic aromatic C—H (derived from CBP unit).

The number average molecular weight of polymer 1 was about 10,000 as determined using polystyrene as a standard.

Synthesis of Charge Transport Material 2

A 200-ml Kolben was charged with 3.2 g (5.5 mmol) of monomer A prepared above, 0.5 g (4.8 mmol) of styrene, and 80 ml of toluene under a nitrogen stream. The mixture was heated on a warm water bath to 80° C., and 0.15 g (0.9 mmol) of azobisisobutyronitrile was introduced into the mixture. A polymerization was allowed to react with stirring for 5 hr. After the completion of the reaction, the reaction solution was allowed to cool. This reaction solution was added dropwise to acetone. The resultant precipitate was collected by filtration and was washed with acetone to give 2.0 g of charge transport material 2 represented by the following formula.

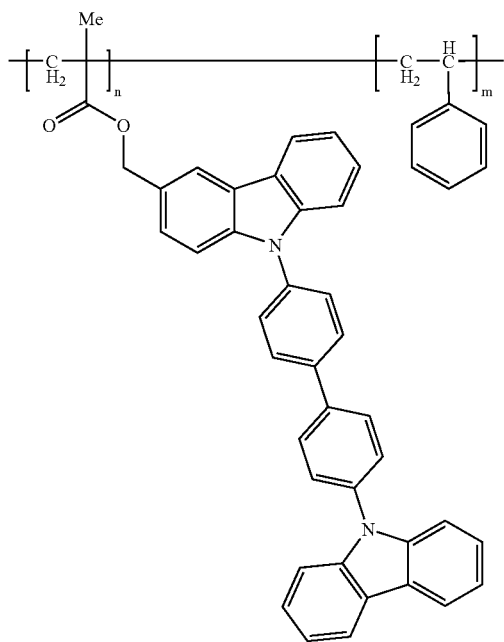

wherein n+m is a number which provides a molecular weight of 7,000.

Figure 3:
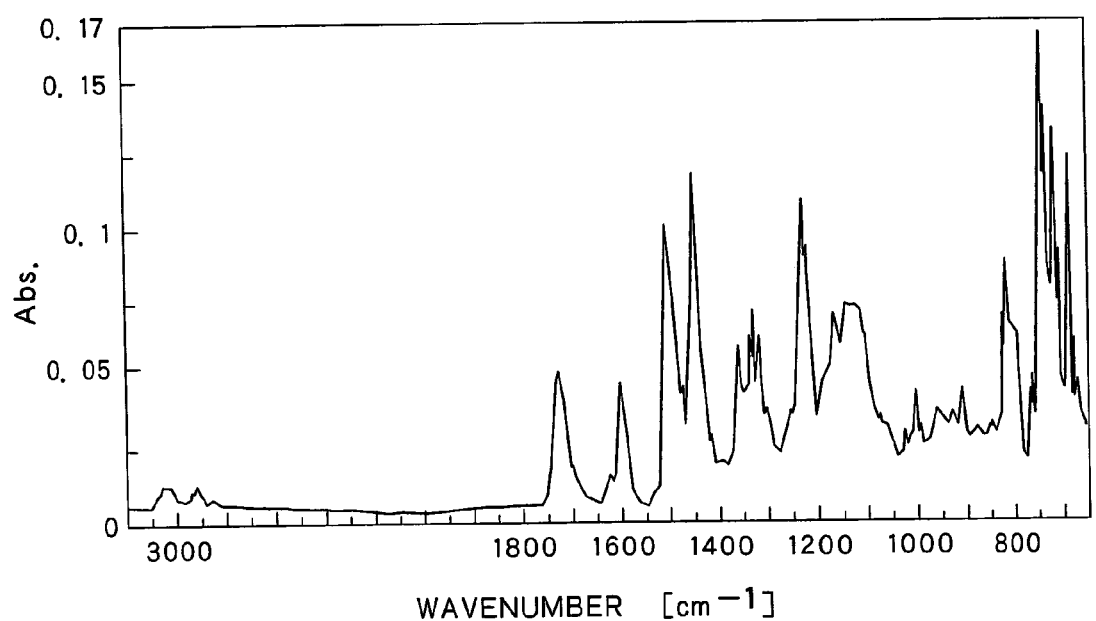
FIG. 3 is an IR spectrum of a charge transparent material 2.

An IR spectrum of the charge transport material 2 is shown in FIG. 3. The IR spectrum of charge transport material 2 had the following main absorption peaks.

3,100–3,000 cm$^{-1}$: stretching of aromatic C—H (derived from CBP unit, styrene unit); 2,922 cm$^{-1}$: stretching of alkane C—H (derived from polymer main chain); 1,725 cm$^{-1}$: stretching of saturated fatty ester C=O; 1,503 cm$^{-1}$: stretching of aromatic C=C (derived from CBP unit, styrene unit); 1,200–1,100 cm$^{-1}$: stretching of saturated fatty ester C—O; 746 cm$^{-1}$: out-of-plane deformation vibration of polycyclic aromatic C—H (derived from CBP unit); 723 cm$^{-1}$: out-of-plane deformation vibration of polycyclic aromatic C—H (derived from CBP unit); and 699 cm$^{-1}$: out-of-plane deformation vibration of monocyclic aromatic C—H (derived from styrene unit).

The number average molecular weight of polymer 2 was about 7,000 as determined using polystyrene as a standard.

Dissolution Test and Film Formation Test

Charge transport material 1 was soluble in an amount of not less than 1% by mass in chloroform, 1,2-dichloroethane, and tetrahydrofuran. Charge transport material 2 was soluble in an amount of not less than 1% by mass in toluene, chloroform, 1,2-dichloroethane, and tetrahydrofuran. Further, charge transport materials 1 and 2, when used with any of the above solvents, could be spin coated on a glass substrate to form an even thin film without doping or any binder.

Measurement of Energy Level

Thin films of charge transport materials 1 and 2 prepared above and a thin film of CBP as a comparative reference material were formed and were measured for their work function and electron affinity. The thin film of CBP was formed by vacuum deposition. The work function was determined with an ultraviolet photoelectron analyzer (AC-1, manufactured by RIKEN KEIKI CO., LTD.) in the air. Next, an absorption spectrum was measured with an ultraviolet-visible absorption spectrum measuring apparatus (MPC-3100, manufactured by Shimadzu Seisakusho Ltd.) to calculate a bandgap value based on the end on the longer wavelength side of the spectrum. The electron affinity was calculated based on the measured work function value and bandgap value.

Charge transport material 1 had a work function value of 5.89 eV and an electron affinity of 2.60 eV. Charge transport material 2 had a work function value of 5.91 eV and an electron affinity of 2.61 eV. These work function and electron affinity values were substantially comparable to the work function value (5.58 eV) and the electron affinity (2.23 eV) of CBP. This demonstrates that charge transport materials 1 and 2 can be coated to form a film while maintaining properties comparable to those of CBP.

The invention claimed is:

1. A charge transport monomer represented by formula (I):

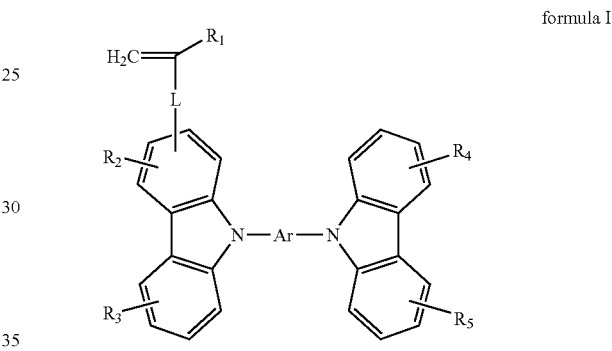

formula I wherein
Ar represents an unsubstituted or substituted arylene group having 6 to 60 carbon atoms involved in conjugation or an unsubstituted or substituted heterocyclic compound group having 4 to 60 carbon atoms involved in conjugation;
L represents a divalent hydrocarbon or hetero-atom-containing hydrocarbon group which may be branched or contain a cyclic structure; and
$R_1$ to $R_5$ each independently represent a group selected from the group consisting of a hydrogen atom, an alkyl group having 1 to 20 carbon atoms, an alkoxy group having 1 to 20 carbon atoms, an aryl group having 6 to 60 carbon atoms, an aryloxy group having 6 to 60 carbon atoms, an arylalkyl group having 7 to 60 carbon atoms, an arylalkoxy group having 7 to 60 carbon atoms, a heterocyclic compound group having 4 to 60 carbon atoms, a cyano group, a nitro group, and a halogen atom.

2. A charge transport material comprising a polymer containing at least one charge transport monomer unit according to claim 1.

3. The charge transport material according to claim 2, wherein the number of said monomer units per molecule of the polymer is 5 to 100,000.

4. A process for producing a charge transport material, said process comprising the step of polymerizing the charge transport monomer according to claim 1 either alone or together with other monomer.

* * * * *